United States Patent [19]

LaForge et al.

[11] Patent Number: 4,665,896
[45] Date of Patent: May 19, 1987

[54] POWER SUPPLY FOR BODY IMPLANT AND METHOD OF USE

[75] Inventors: David H. LaForge, Kensington; James Lee, Benicia, both of Calif.

[73] Assignee: Novacor Medical Corporation, Oakland, Calif.

[21] Appl. No.: 757,786

[22] Filed: Jul. 22, 1985

[51] Int. Cl.[4] .............................................. A61F 1/24
[52] U.S. Cl. .............................. 128/1 D; 128/419 PS; 128/419 F
[58] Field of Search ................. 128/1 D, 1 R, 419 PS, 128/419 R, 419 F; 623/3

[56] References Cited

U.S. PATENT DOCUMENTS

| | | |
|---|---|---|
| 3,195,540 | 7/1965 | Walker ........................... 128/419 PS |
| 3,942,535 | 3/1976 | Schulmon ....................... 128/419 PS |
| 4,143,661 | 3/1979 | LaForge et al. . |
| 4,275,739 | 6/1981 | Fischell ........................... 128/419 PS |
| 4,384,829 | 5/1983 | Conley et al. . |
| 4,457,673 | 7/1984 | Conley et al. . |
| 4,548,208 | 10/1983 | Niemi ............................. 128/419 F |

FOREIGN PATENT DOCUMENTS

| | | |
|---|---|---|
| 2720331 | 11/1978 | Fed. Rep. of Germany ...... 128/419 PS |
| 87174 | 5/1966 | France ........................... 128/419 PS |

OTHER PUBLICATIONS

Donaldson, "Medical and Biological Engineering and Computing" vol. 23, No. 3, May 1985, p. 291.
Schuder, J. C., and Stephenson, H. E., "Energy Transport to a Cell which Circumscribes a Ferrite Core that is Implanted Within the Body", Dept. of Surgery, University of Missouri, Columbia, MO 1964.
Bruesdchke, E. E., Uretz, E. F., & Hauser, R. G., "Test and Evaluation of Transformer Study", I.I.T. Research Inst., NO1-9-2125-3, Jan. 1975.

Primary Examiner—William E. Kamm
Attorney, Agent, or Firm—Fitch, Even, Tabin & Flannery

[57] ABSTRACT

An implanted blood pump system is described wherein power for driving the pump is provided by a transcutaneous transformer having an external primary winding and an implanted secondary winding. Control of the driving voltage to the pump is provided by an implanted shunt regulator. Voltage applied to the primary winding is controlled in accordance with the power factor sensed in the primary winding.

10 Claims, 4 Drawing Figures

POWER SUPPLY FOR BODY IMPLANT AND METHOD OF USE

This invention relates to electric power supplies, and more particularly to a power supply for an electrical circulatory support device which is implanted within a living body.

The relatively high amount of power required by circulatory support devices (blood pumps), such as a partial or total artificial heart, has rendered most implantable, self-sufficient energy sources inapplicable, such as those used for a pacemaker. Only high-power, radioisotope heat sources have held any promise of sustained outputs of several watts; however, the utilization of such an energy source has been complicated by its inherent need for a miniature, high efficiency heat engine, as well as by serious radiation-related problems. All other practical approaches to powering an artificial heart or circulatory assist system of some type necessarily depend on a more or less continuous flow of energy from outside the body. Results of efforts at infection-free maintenance of long-term percutaneous connections are discouraging and thus highlight the desirability, at least for the long term, of powering such an implanted device though intact skin.

One of the earliest approaches to the transmission of energy across intact skin involves the generation of a radio frequency field extending over a substantial area of the body, such that significant power could be extracted from coils located in the vicinity of the implanted power-consuming device itself. Placement of substantial amounts of ferrite materials within such coils to permit the capture of a greater proportion of the incident field was also investigated, as reported in the article by J. C. Schuder, et al. in the 1964 Transactions ACEMB. However, difficulty has been experienced in reconciling the conflicting requirement of magnetic circuit geometry with a surgically feasible, variable tissue structure. In another proposed alternative design, a secondary coil is implanted in such a manner that the center of the coil remains accessible through a surgically constructed tunnel of skin; however, such devices have not yielded satisfactory performance. Predominant failure modes include necrosis of the skin tunnel tissue caused by mechanical pressure and excess heat generation—see the 1975 report of I.I.T. Research Institute, by Brueschke, et al., N.I.H. Report No. N01-HT-9-2125-3, page 25.

In U.S. Pat. No. 4,143,661, issued Mar. 13, 1979, assigned to the assignee of the present invention, a so-called belt skin transformer (BST) system is described in which a secondary coil is implanted just below the skin of the abdomen or the thigh so that it encircles the patient's torso or leg along most of the length of the coil and lies at a location close to the skin's surface. A primary coil, in the form of an encircling belt which is greater in width than the secondary implanted coil, fits around the patient in the region just radially outward of the secondary coil. Power is supplied to the primary coil, which is then inductively coupled transcutaneously to the secondary coil, which in turn operates the device and charges and implanted storage battery.

Naturally, proper circuit design in a BST system requires regulation of the voltage applied to the load or blood pump. Although a variety of regulatory expedients are known in the prior art, the uniqueness of the transcutaneous transformer arrangement employed in systems of this type makes the prior art of little value in predicting ideal arrangements. It has been found that a two tier regulation scheme, employing an internal regulator for driving the blood pump itself, and employing an external regulator for controlling voltage input to the primary winding, is particularly desirable. Coordination of the two regulators may, of course, be achieved by suitable telemetry signals. However, such telemetry circuitry adds additional expense, complexity, and unreliability factors to the system.

It is an object of the present invention to provide an improved implanted blood pump system and method for operating same.

Another object of the invention is to provide an implanted blood pump system in which a highly effective means of voltage regulation is achieved.

Another object of the invention is to provide an improved implanted blood pump system which coordinates regulation of the voltage applied to the system in accordance with load demands and without the need for telemetry monitoring.

Other objects of the invention will become apparent to those skilled in the art from the following description, taken in connection with the accompanying drawings wherein.

Very generally, in the implanted blood pump system of the invention, power for driving the pump is provided by a transcutaneous transformer having an external primary winding and an implanted secondary winding and an implanted shunt regulator. The secondary winding applies driving voltage to the pump which is controlled by the shunt regulator. The voltage applied to the system is regulated by sensing the power factor in the primary and comparing the power factor to a predetermined power factor level selected to correspond with a desired driving voltage. The voltage level in the primary winding is adjusted to substantially equalize the sensed power factor and the predetermined power factor level.

Figure 1:
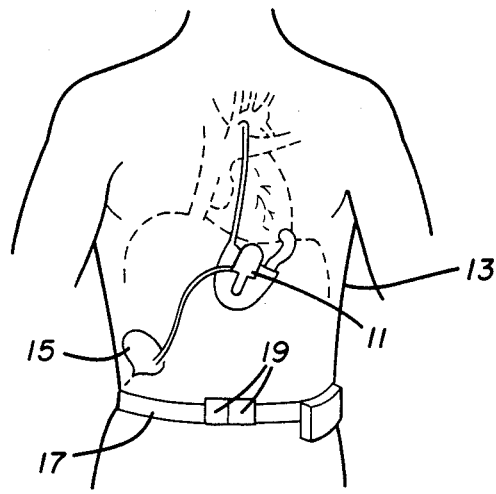
FIG. 1 is a diagrammatic depiction of the implanted portion of a power supply system shown in conjunction with a circulatory blood pump within a living human.

Referring now more particularly to FIG. 1, a blood pump in the form of a left ventricular assist device 11 is depicted implanted within the body 13 of a patient. The device is preferably of the type shown and described in U.S. Pat. Nos. 4,457,673 and 4,384,829. The system also includes an implanted module 15 that includes electronic rectifying and control components and a standby storage battery.

Figure 2:
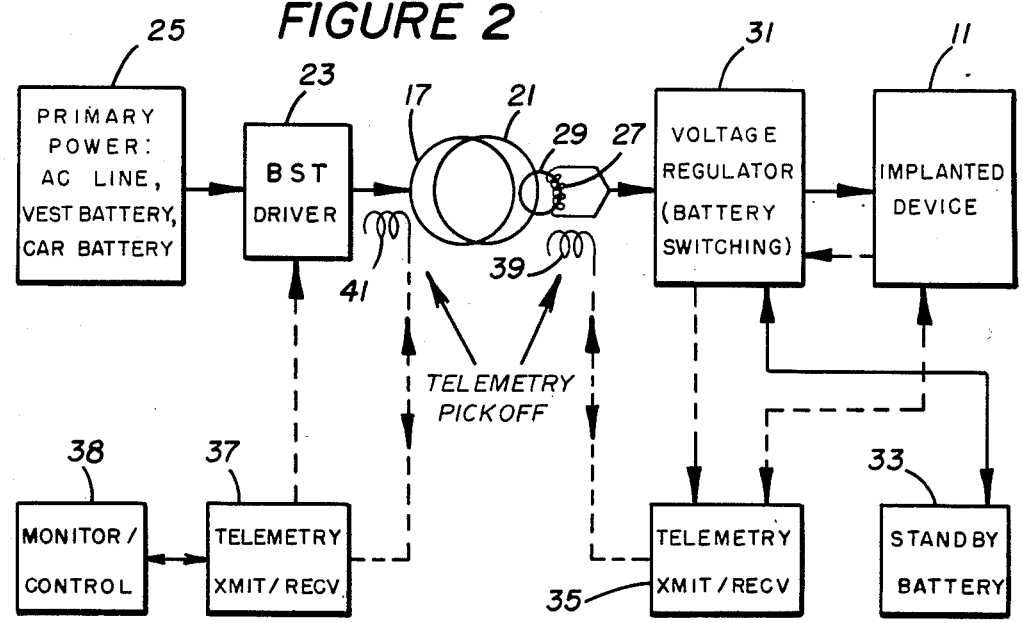
FIG. 2 is a block diagram of the system illustrated in FIG. 1.
Figure 3:
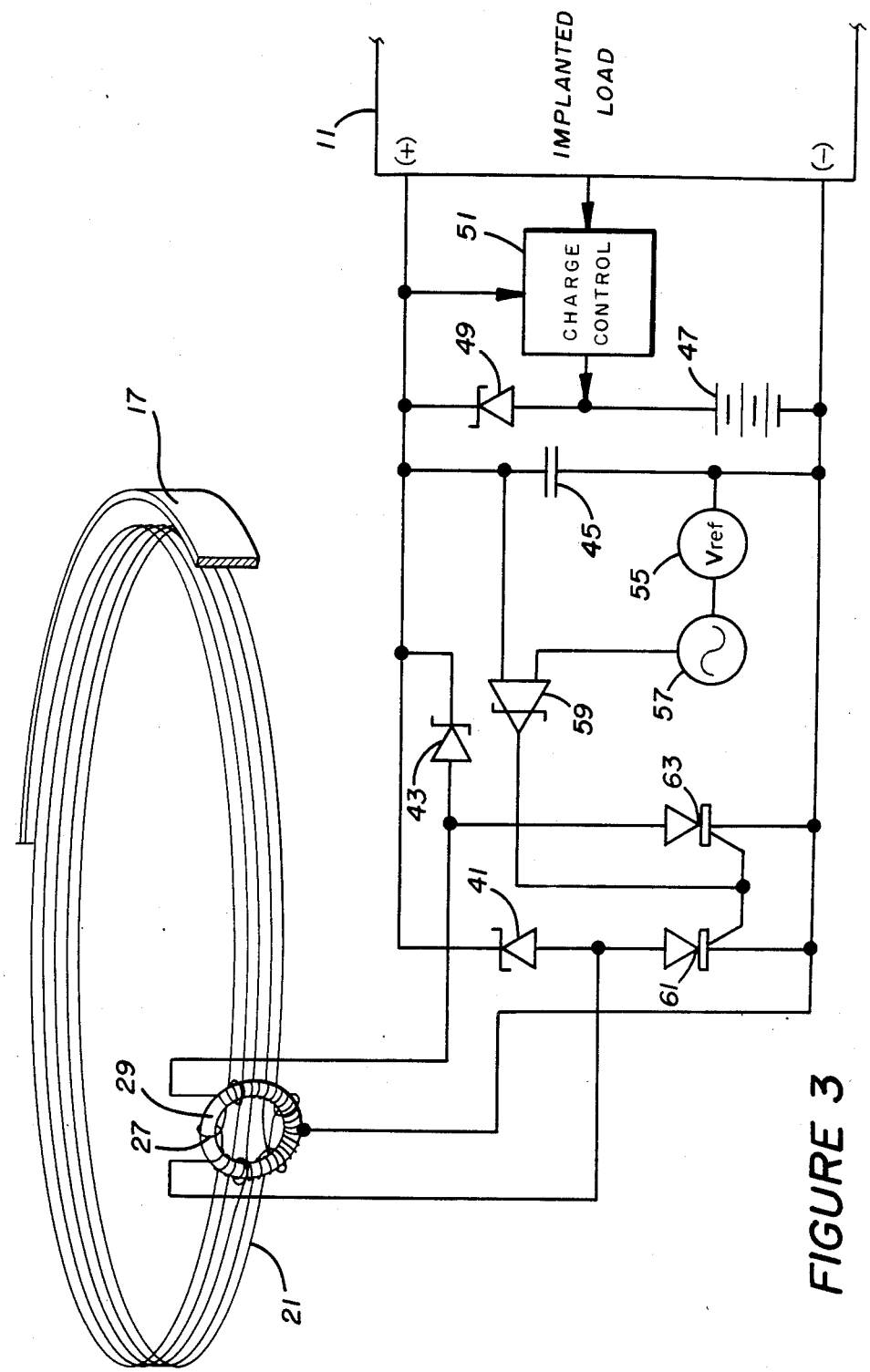
FIG. 3 is a schematic diagram illustrating the secondary transformer of the system of FIG. 1 connected to rectifier, voltage regulator, and other implanted elements including the blood pump itself (implanted load)

The system is powered and charged via coupling to a primary coil which is constituted by an outer belt 17 having a disconnectable belt buckle 19. A secondary coil, not visible in FIG. 1, but designated as 21 in FIGS. 2 and 3 is implanted in the abdomen about the waist. The primary coil 17 overlaps the secondary coil 21 and, when positioned about the waist of a wearer, is inductively coupled to the secondary coil 21. Because of the relatively large diameter of the two air core coils, a very high magnetic coupling coefficient is achieved in an overall light weight iron free system.

Referring now to FIG. 2, the belt skin transformer (BST) comprising the primary winding 17 and the secondary winding 21 is driven by a BST driver, 23, more fully explained below. Power for the BST driver may be supplied from any suitable source, such as a normal alternating current line, a vest battery, a car battery, etc. and is indicated generally by the element 25 in FIG. 2. As may be seen in FIG. 2 and as is more specifically illustrated in FIG. 3, the secondary winding which has a plurality of parallel wires wound in a single turn with respect to the primary, is coupled to a tertiary winding 27. It is preferable for all secondary windings to be parallel because: (1) it is more reliable because of its redundancy; (2) the greatest potential between windings and tissue is less than one volt; (3) a simple single circuit connector can be used; (4) there is no danger of short circuits between windings of different potential. It is preferable to space the wires for flexibility and because they thus form a wide "current sheet" which reduces formation of parasitic leakage fields (as around a small wire) which would fail to couple with the primary belt.

Both windings 21 and 27 are wound on a common toroidal core 29. This particular design is useful in functioning as a current equalizing device. The separate equivalent transformers of the wires of the single-turn coil 21 and the multi-turn coil 27 are interleaved in windings equally spaced around the core 29. Since these transformers are physically parts of the same core, they exhibit a very high coupling. In fact, their individual coupling is typically about 98%. Intercoupling between the windings, however, is typically only about 85%. Hence, there is a tendency toward a current equalization and thus a cancelling of local fields within the belt. This eliminates conductor degradation and electrical losses which might be encountered in the event of unbalanced currents in the parallel wires of the single-turn coil 21.

Output from the winding 27, which will be more specifically described below, is applied to a voltage regulator and battery switching circuit 31 which, in turn, drives the implanted device 11. A standby battery 33 is also used for periods in which the external power supply in the form of the BST driver 23 is temporarily disconnected. Suitable implanted telemetry circuitry 35 and external telemetry circuitry 37 are coupled by telemetry pick-off units 39 and 41, respectively, in order to permit monitoring and control of the implanted device by means of the monitor/control unit 39.

The implanted load or heart assist device 11 is driven from the tertiary winding 27 by a pair of Schottky diodes 41 and 43, which are connected as full-wave rectifiers to the implanted load 11. The Schottky diodes are used to minimize voltage drop and may be of the type 1N5825. The output voltage of the rectifier is smoothed by a capacitor 45 connected across the load. An auxiliary battery 47 is provided connected through a diode 49 across the load to supply auxiliary or standby power to the load. A switch and current regulating charge control 51 is provided for the battery 47 and may be of any suitable design to charge the battery from the positive portion of the rectified signal. Suitable signals may be developed from the implanted device to switch the charge control on and off. If the positive power to the implanted load drops below that of the battery 47, the diode 49 conducts, providing the standby power to the load.

In order to internally regulate the power provided to the implanted load, a shunt regulator is provided. The shunt regulator includes a reference voltage source 55 connected through a low voltage, low frequency oscillator 57 (sometimes known as a "dither") to a voltage comparator amplifier 59. The voltage output of the voltage comparator 59 is connected to the gates of a pair of SCR switches 61 and 63. The switches are connected across respective portions of the tertiary winding 27 and operate to shunt the output thereof, when the switches are closed, from the rectifying diodes 41 and 43, thus blocking the flow of power to the smoothing capacitor 45. During such periods the implanted load is supplied with power by discharge of the smoothing capacitor.

In operation, the shunt regulator is configured such that the switches 61 and 63 remain open when the voltage output of the rectifiers 41 and 43 is high enough to drive the load 11 and charge the battery 47, when applicable. This voltage, which is near the reference level 55, is sensed by the voltage comparator 59. When the voltage output of the diodes 41 and 43 exceeds the reference level, the voltage comparator 59 provides an output to the gates of the switches 61 and 63, turning the switches on (i.e. closing the switches). Under such circumstances, the tertiary winding 27 and hence the secondary winding 21 is effectively shorted. The frequency at which the switches 61 and 63 are operated is selected to be much lower than the power frequency in the tertiary winding 27 to minimize switching losses, simplify control and reduce undesirable harmonic generation. The oscillator 28 assists in the maintenance of the low frequency switching by causing the shunt regulator switching to occur at a predetermined fixed frequency, for example about 1 kHz, which simplifies the primary circuit regulator. As an alternative, the comparator 59 may be provided with a switching histeresis or dead band in accordance with known practice.

Figure 4:
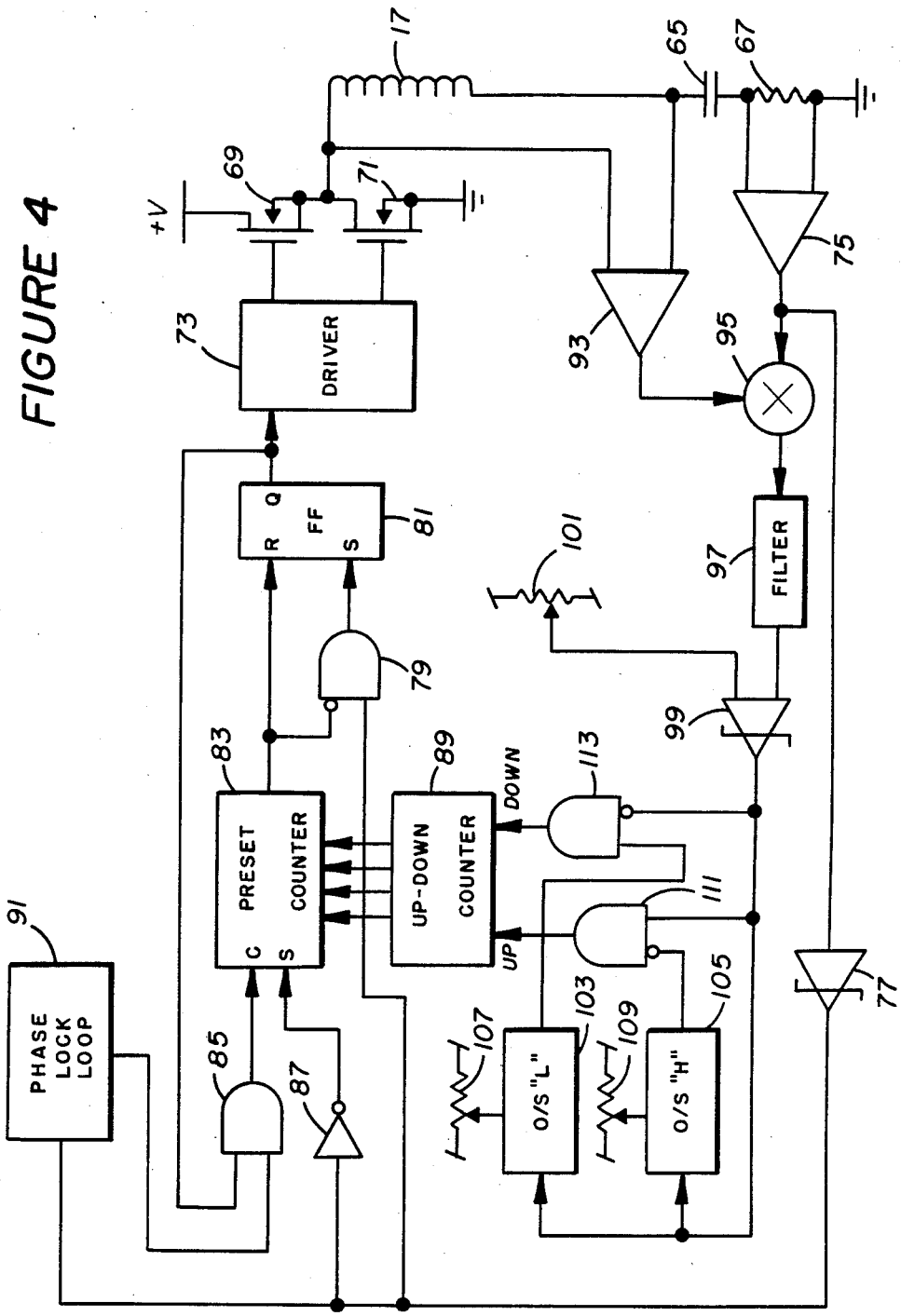
FIG. 4 is a schematic diagram of the primary winding power circuit utilized in the system of FIG. 1.

Referring now to FIG. 4, the components of the BST driver 23 are illustrated. The primary winding 17 is connected via a capacitor 65 and series resistor 67 to ground. A pair of power switches couple a source of positive voltage (for example a 12 volt automotive battery), or to ground. The power switches 69 and 71 are series connected with their junction being connected to one end of the primary winding 17. The primary winding 17 and the series capacitor 65 and resistor 67 form a series resonant circuit and the frequency at which the primary winding 17 is driven is determined by this resonance. Typically, this frequency will be approximately 80 kHz and will change in response to respiration and other mechanical factors effecting the inductance of the primary winding 17. Phase lock of the driver circuit to the primary resonance is accomplished by switching the power circuit via the power switches 69 and 71 to the positive power source when zero current is detected. This also facilitates self starting of the system.

In order to drive the switches 69 and 71 at the desired frequency, a driver circuit 73 is provided. This driver circuit, which may be any suitable amplifier driver, is coupled to the gates of the switches 69 and 71 and is controlled such that the duration of the on time of the power switches 69 and 71 determines the duty cycle and therefore the total power which is applied to the primary winding 17.

In order to detect the current in the primary winding 17, the resistor 67 is connected to an amplifier 75 which develops a signal proportional to the current in the primary winding 17. This signal is applied through a comparator 77 and through a gate 79 to a flip-flop 81. The comparator 77 is a digital output comparator which develops a digital signal which is a square wave at a frequency which is in phase with the current in the primary winding 17. This digital signal sets the flip-flop 81 through the gate 79, initiating a drive pulse from the flip-flop 81 to the driver 73. The driver circuit 73 operates to amplify this pulse to control the switches 69 and 71 and to ensure that both switches cannot conduct simultaneously.

In order to control the width of the pulse output in the primary winding 17, the relative width of the pulse applied from the flip-flop 81 to the driver 73 is controlled. Since the power frequency may change, it is preferable to generate a pulse having a certain fraction of the period $T=1/F$, rather than a pulse of a fixed duration. In order to do this, a reference frequency is generated, for example a reference of $32 \times F$. To this end, a preset counter 83 is provided connected to the gate 79 and the flip-flop 81. The counter, which may for example be industry type 4510, begins to count at the reference frequency (in the Example 32F) when the gate 85, connected to the input of the preset counter 83, is enabled. When the preset count is reached, the flip-flop 81 is reset, ending the pulse to the driver 73 and thus turning off the power switches 69 and 71. The gate 79 operates to prevent the flip-flop 81 from turning on again, even if the signal output of the comparator 77 is still high.

When the signal output of the comparator 77 is low, an inverter 87, connected to the preset counter 83, resets the preset counter 83 to the preset number. This preset number may be derived from an up-down counter 89, connected to the preset counter 83 and which may also be of the industry type 4510. On the basis of a reference frequency of 32 times the resonant frequency, the counter 83 may be set for a maximum count of 15. Thus, the 16th pulse will terminate the output of the driver 73. In this example, since the counter 83 is counting at a frequency of 32 times the resonant frequency, the greatest possible width of the output pulse is 50% of the period $T=1/F$, corresponding to a full power square wave drive. Lower preset counts, of course, give narrower pulses of lower power level.

In order to derive the reference frequency from the signal output of the comparator 77, a conventional phase lock loop 91 is utilized. Phase lock loops are generally well known in the art and may employ a simple binary counter and loop filter combined with other appropriate elements in a single chip, such as industry type 215 or 565.

Voltage in the primary winding 17 is sensed by a differential amplifier 93. The amplifier 93 generates an analog of the voltage in the primary winding 17 which is then applied to a multiplier 95 (for example, type 1496). The output from the amplifier 75 is also applied to the multiplier 32. The multiplier acts as a phase sensitive detector and its output has a substantial average value (DC component) if and only if the impedance of the primary winding 17 has a substantial resistive component. The output of the multiplier 95 is fed through a low-pass filter 97 (which removes product components of the resonant frequency of the primary winding 17 and higher frequencies) to a comparator 99. The comparator 99 is connected to an adjustable offset pot 101 which permits the threshold of the comparator 99 to be set sufficiently high as to reject output from the filter 97 resulting from noise and power dissipated in the resistance of the belt skin transformer.

The output of the comparator is applied to two monostable multivibrators 103 and 105. Each of the monostable multivibrators 103 and 105 produces pulses of adjustable length "L" and "H", respectively. Each multivibrator is connected to a variable resistor, 107 and 109, respectively, which constitute part of the timing circuits of the multivibrators. For example, the multivibrators could be the two halves of a type 4528 chip. The difference in settings between L and H serves as a refractory or dead zone to help reject noise and prevent the implanted and primary regulators from interacting. The multivibrators control a pair of gates 111 and 113, respectively, which are connected to the up-down counter 89 and serve, as will be explained, to adjust the up-down counter 89 and therefore the preset counter 83 to control the width of the pulses in the primary winding 17.

Referring now more particularly to the operation of the device, as previously mentioned, when the shunt regulator in the implanted circuitry is open, the load which the primary winding 17 sees is primarily resistive. However, once the shunt regulator switches close, the load becomes primarily inductive. During the time that this shunt regulator is conducting current, current is circulating unproductively in the coils of the belt skin transformer, thus contributing to resistive losses. It is therefore desirable to adjust the power level in the primary winding as low as possible consistent with maintaining secondary shunt regulator control. In accordance with the invention, the conduction angle or power factor in the primary winding 17 is sensed and the duty cycle of the primary drive pulse is controlled accordingly. Power factor is defined as cos 0 where 0 is the phase angle between current and voltage. A power factor of unity indicates the load is purely resistive.

More particularly, the multiplier 95 operates to compare and thus detect the phase relation between voltage and current in the primary winding 17. As such, the output signal of the multiplier 95 is high when the switches 61 and 63 are open reflecting a resistive load, and is low when the switches 61 and 63 are closed, reflecting an inductive load. The output of the multiplier 95 is therefore a series of pulses of a frequency F fixed by the oscillator 57 and having a duty factor equal to the load conduction factor on the shunt regulator 61, 63.

Each positive ongoing edge of the pulses represented by the output of the multiplier 95 triggers the monostable multivibrators 107 and 109. The output is a pair of pulses of length L and H, respectively, the length of which is set by adjustment of the variable resistors 107 and 109. For example, if the frequency of the output of the multiplier 95 is 1 kHz, corresponding to a pulse period in the primary winding 17 of 1 millisecond, H might be set to 0.9 milliseconds and L might be set to 0.6 milliseconds. The difference between L and H, namely, 0.3 milliseconds, serves as the refractory or dead zone which minimizes interaction between the implanted and external regulators.

If the duration of each pulse in the output of the multiplier 95 is less than H but greater than L, the implanted shunt regulator is considered within its ideal operating range (60% to 90% load conduction). Neither of the gates 111 or 113 produce outputs. The number in the up-down counter 89 is unchanged and therefore the duty cycle of the pulse in the primary winding 17 is constant. If pulse H ends before the end of the pulse from the multiplier 95, the gate 111 will produce an output which adds one count to the up-down counter 89 for each occurrence. Upon such occurrence, the width of the pulses in the primary winding 17 is increased, delivering more power to the implanted circuitry. On the other hand, if the pulse from the multiplier 95 ends before the pulse L, the gate 113 will produce an output which decreases the count in the up-down counter 89 and thus reduces the width of the pulses applied to the primary winding 17. By such means, the power level reaching the secondary of the belt skin transformer is controlled so that the implanted regulator components can efficiently stabilize the belt skin transformer output voltage.

It may be seen, therefore, that the system and method of the invention operate to effectively regulate the power levels applied to the implanted blood pump system described. A two tier regulation scheme is employed wherein a shunt regulator in the implanted circuit controls the load voltage and wherein a primary regulator senses the conduction angle of the shunt regulator and adjusts the primary power level, by changing the duty factor of the primary drive pulse. Accordingly, unproductive circulation of current in the transcutaneous transformer and consequent resistive losses are minimized. As a consequence, close regulation of the power to the implanted device is achieved without the necessity of elaborate telemetry control.

Various modifications of the invention in addition to those shown and described herein will become apparent to those skilled in the art from the foregoing description and accompanying drawings. Such modifications are intended to fall within the scope of the appended claims.

What is claimed is:

1. In an implanted blood pump system wherein power for driving the pump is provided by a transcutaneous transformer having an external primary winding means and an implanted secondary winding means and shunt regulator means for controlling the driving voltage applied to the pump, a method for regulating the driving voltage applied to the primary winding means, comprising, sensing the power factor in the primary winding means, comparing the sensed power factor to a predetermined power factor level selected to correspond with a desired pump driving voltage, and adjusting the voltage level in the primary winding means to substantially equalize the sensed power factor and the predetermined power factor level.

2. A method according to claim 1 wherein the power factor in the primary winding means is sensed by comparing the voltage and the current signals in the primary winding means and producing a control signal which is responsive to operation of the shunt regulator means.

3. A method according to claim 1 wherein the voltage level in the primary winding means is adjusted by varying the width of pulses applied thereto.

4. An implantable blood pump system comprising, an implanted pump and a transcutaneous transformer having an external primary winding means and an implanted secondary winding means, said system further comprising implanted shunt regulator means for controlling the driving voltage applied to said pump, means for sensing the power factor in said primary winding means, means for comparing the sensed power factor to a predetermined power factor level selected to correspond with a desired driving voltage for said pump, and means for adjusting the voltage level in said primary winding means to substantially equalize the sensed power factor and the predetermined power factor level.

5. Apparatus according to claim 4 wherein said power factor sensing means includes means for comparing the voltage and the current signals in said primary winding means and for producing a control signal which is responsive to operation of said shunt regulator means.

6. Apparatus according to claim 4 including means for varying the width of pulses applied to said primary winding means to control the voltage level therein.

7. Apparatus according to claim 4 wherein said shunt regulator means include switching means connected across said secondary winding means, and voltage comparator means for turning on said switching means when the voltage across said secondary winding means exceeds a predetermined level.

8. A system according to claim 4 including an implanted battery connected to said pump and further including means for connecting said battery to said pump when the voltage across said secondary winding means falls below a preselected level.

9. Apparatus according to claim 4 wherein said secondary winding means include first and second inductively coupled winding means, each of said first and second inductively coupled winding means being wound on a common toroidal core.

10. Apparatus according to claim 9 wherein the said first winding means comprise a plurality of parallel first windings in which the currents are made equal in addition to being coupled to the second winding means, by being disposed about said toroidal core with equal spacing.

* * * * *